United States Patent [19]

Brown-Skrobot et al.

[11] Patent Number: 4,975,217

[45] Date of Patent: Dec. 4, 1990

[54] VIRUCIDAL COMPOSITION, THE METHOD OF USE AND THE PRODUCT THEREFOR

[75] Inventors: Susan K. Brown-Skrobot, Hamilton Square, N.J.; Shafi U. Hossain, Roswell; Kenneth R. Smith, Marietta, both of Ga.; Cary K. Kuenn, Appleton, Wis.

[73] Assignee: Kimberly-Clark Corporation, Neenah, Wis.

[21] Appl. No.: 144,850

[22] Filed: Jan. 15, 1988

Related U.S. Application Data

[63] Continuation-in-part of Ser. No. 447,581, Dec. 13, 1982, Pat. No. 4,828,912, which is a continuation-in-part of Ser. No. 392,781, Jun. 30, 1982, abandoned, which is a continuation-in-part of Ser. No. 284,688, Jul. 20, 1981, abandoned.

[51] Int. Cl.$^5$ .............................................. C11D 9/50
[52] U.S. Cl. .................................... 252/107; 424/404; 514/578; 514/711; 514/142
[58] Field of Search ........................ 424/404; 252/107; 514/711, 578, 942

[56] References Cited

U.S. PATENT DOCUMENTS

| | | | |
|---|---|---|---|
| 3,023,144 | 2/1962 | Greathouse et al. | 167/58 |
| 3,057,467 | 10/1962 | Williams | 206/46 |
| 3,244,636 | 4/1966 | Reller et al. | 252/107 |
| 3,278,370 | 10/1966 | McCoy et al. | 167/60 |
| 3,408,298 | 10/1968 | Baraville | 252/107 |
| 3,836,044 | 9/1974 | Tilp et al. | 221/55 |
| 3,969,258 | 7/1976 | Carandang et al. | 252/106 |
| 4,017,002 | 4/1977 | Doyle et al. | 221/63 |
| 4,045,364 | 8/1977 | Richter | 252/106 |
| 4,105,782 | 8/1978 | Yu et al. | 424/283 |
| 4,105,783 | 8/1978 | Yu et al. | 424/283 |

OTHER PUBLICATIONS

Cowles, P. B., "Alkyl Sulfates: Their Selective Bacteriostatic Action", *Yale Journal of Biology and Medicine*, 11, 33-38, (1938).

Archiv fur Lebensmittelhygiene, 29, 81-120 (1978).

Dychdala, G. R., "Surface-Active Agents: Acid-Anionic Compounds", Disinfection, Sterilization, and Preservation, S. Block (ed.), 3rd Ed., pp. 330-333, (1983).

Newton, B. A., "Surface-Active Bactericides", *Symposium for the Society for General Microbiology*, No. 8, pp. 62-93, (1958).

Sobel, J. D. et al., "Nosocomial *Pseudomonas cepacia* Infection Associated with Chlorhexidine Contamination", *Am. J. Med.*, 73, 185-186, (1982).

Fox, J. G., et al., "Nosocomial Transmission of *Serratia marcesens* in a Veterinary Hospital due to contamination by Benzalkonium Chloride", *J. of Clin. Microbiol.*, 14, 157-f160, (1981).

McBride, M. E., "Microbial Flora of In-use Soap Products", *Appl. and Environ. Microbiol.*, 48, 348-341, (1984).

Marrie, T. J., and Costerton, J. W., "Prolonged Survival of *Serratia marcesens* in Chlorhexidine", *Appl. and Environ. Microbiol.*, 42, 1093-1102, (1981).

Draize, J. H., et al., "Methods for the Study of Irritation and Toxicity of Substances Applied Topically to the Skin and Mucous Membranes", *Journal of Pharmacology and Experimental Therapeutics*, 82, 377-390, (1944).

Aly, R. and Maibach, H. I., "A Comparison of the Antimicrobial Effect of 0.5% Chlorhexidine (HIBISTAT®) and 70% Isopropyl Alcohol on Hands Contaminated with *Serratia marcescens*", *Clin. and Experi. Derm.*, 5, 197-201, (1980).

Hart, J. R., "Sarcosinate Surfactants in Skin Cleansers", *Cosmetic technology*, Jan. 1980.

Baker, Z., et al., "The Bactericidal Action of Synthetic Detergents", *Journal of Experimental Medicine*, 74, 611-621, (1941).

"Sagrosept Cloths", Schulke and Mayr GmbH, Robert-Kock Str. 2, 2000 Noderstedt, West Germany.

*Primary Examiner*—James J. Bell
*Attorney, Agent, or Firm*—William D. Herrick; William E. Maycock

[57] ABSTRACT

Germicidal compositions for direct application to human skin are provided. The compositions include an organic acid, e.g., malic acid, and an anionic surfactant, e.g., a sodium alpha-olefin sulfonate, as active ingredients, and can optionally include an alcohol, e.g., specially denatured ethyl alcohol, as an additional active ingredient. When formulated as soaps and lotions, the compositions have been found to produce more than a 2.0 log reduction in bacteria applied to skin.

20 Claims, No Drawings

VIRUCIDAL COMPOSITION, THE METHOD OF USE AND THE PRODUCT THEREFOR

CROSS REFERENCE TO RELATED APPLICATIONS

This application is a continuation-in-part of U.S. patent application Ser. No. 447,581 filed Dec. 13, 1982, now U.S. Pat. No. 4,828,912 which is a continuation-in-part of U.S. patent application Ser. No. 392,781 filed June 30, 1982, now abandoned which is a continuation-in-part of U.S. patent application Ser. No. 284,688 filed July 20, 1981, now abandoned.

BACKGROUND OF THE INVENTION

1. Field of the Invention

This invention relates to a class of virucidal compositions highly efficacious against common respiratory viruses such as rhinoviruses, parainfluenza viruses, and adenoviruses and the methods and products utilizing such compositions. In particular, the invention relates to a novel type of virucidal composition which can be applied to a variety of substrates or carriers such as cellulosic webs, nonwoven structures, and textile-based materials. In addition, the class of virucidal compositions comprising this invention may also be incorporated into nasal sprays, facial creams, hand lotions, lipsticks, and similar cosmetic preparations. The compositions may also be used as ingredients in kitchen and bathroom cleansers, furniture and floor polishes, and similar household preparations. Along these same lines, the compositions can be used in hand-washing soaps, soapy lotions, and "wet" wipe type products, e.g., products of the type shown in U.S. Pat. Nos. 3,057,467, 3,836,044 and 4,017,002. In addition to their virucidal activity, the compositions of the invention have general germicidal activity, that is, in addition to viruses, the compositions also kill bacteria and yeasts.

Virologists knowledgeable in the field of respiratory viruses generally agree that rhinoviruses, influenza viruses, and adenoviruses are among the most important group of pathogenic agents which cause respiratory illnesses. Rhinoviruses, in particular, are thought to be the principle causative agent of what is generally known as "the common cold".

Rhinovirus, which causes cold symptoms, belongs to the picornavirus family. This family lacks an outer envelope, and therefore, is characterized as "naked viruses". Although more than 100 different antigenic types of rhinoviruses are known, they share certain centrally important attributes. For instance, all are acid labile, and all contain single-stranded RNA (ca. $2.6 \times 10^6$ daltons). All are difficult to inactivate by common germicides such as quaternary ammonium compounds.

Adenoviruses include more than thirty antigenic types. When they invade the respiratory tract, they cause inflammation of the tissues leading to symptoms of pharyngitis, bronchitis, etc. While most adenovirus infections occur in childhood, infections of adults are far from uncommon. Like rhinoviruses, adenoviruses lack an envelope, (i.e. naked) but the adeno-nucleus, in contrast to the rhino-nucleus, contains a double-stranded DNA, and is not characterized as acid labile. Adenoviruses are unusually resistant to inactivation.

Parainfluenza viruses, which belong to the paramyxovirus family, play an important role in the occurrence of lower respiratory diseases in children and upper respiratory diseases in adults. The parainfluenza viruses are RNA-containing viruses endowed with an ether-sensitive, lipoprotein envelope surrounding the nucleocapsid. These viruses are resistant to inactivation by carboxylic acids in low concentrations.

Recent work by Dick and others (Dick, E. C. and Chesney, P. J., "Textbook of Pediatric Diseases", Feigin, R. D. and Cherry, J. D. ed., Vol. II, p. 1167 (1981) W. B. Saunders Pub. Co., Phila., PA) has thrown considerable light on the mode of transmission of respiratory diseases caused by rhinoviruses. Although the exact mode of transmission of respiratory diseases is not fully understood, field studies by the above investigators have provided persuasive evidence that effective transmission of diseases such as common colds usually requires close association or contact—direct or indirect—between the infected subject and the potential victim. (Indirect contact may be looked upon as contact occurring via an intervening surface, e.g., table top, door knob, etc.). Thus, it may be possible to interrupt the chain of infection and reduce its potential to spread if the viruses can be rendered ineffective as they emerge from an infected person's nose or mouth by immediate exposure to a virucidal agent. Moreover, after emergence, viruses which may ensconce themselves on the infected person's face or hands may also be "killed" if a suitable virucidal agent is quickly brought into contact with the appropriate anatomical surface, i.e., face, hands, etc. A facial tissue, containing a fast-acting, efficacious virucidal composition would offer a simple means of accomplishing the tasks mentioned above.

A long-felt need has existed for a safe and inexpensive virucidal agent effective against common respiratory viruses. Simple household germicides are not effective against rhino- and adenoviruses.

2. Description of the Prior Art

U.S. Pat. No. 4,045,364 to Richter discloses a disposable paper impregnated with an iodophor (i.e. iodine and a carrier) having germicidal properties and useful as a pre-wash in a surgical scrub routine. The patentee discloses that the stability of the iodophor is enhanced at a lower pH and that small quantities of weak organic acids such as citric acid or acetic acid can be added to achieve pH control. U.S. Pat. No. 3,881,210 to Drach et al. describes a pre-moistened wiper for sanitary purposes which can include a bactericide. U.S. Pat. No. 3,654,165 to Bryant et al. discloses a cleaner/sanitizer for wiping purposes including iodine providing bactericidal action. U.S. Pat. No. 3,567,118 to Shepherd et al. discloses a fibrous material for cleaning purposes having a coating of a hydrophilic acrylate or methacrylate containing, inter alia, a bactericide. German product brochure entitled "Sagrosept ® Cloths", Schulke and Mayr GmbH, Robert-Koch-Str. 2, 2000 Norderstedt, West Germany, describes wet disinfection and cleaning cloths containing 2-propanol, 1-propanol, benzoic acid and lactic acid as active ingredients. See also German Patent No. 1,924,490.

While the prior art has disclosed that iodine compositions and products have a wide-spectrum virucidal effect, there has yet to be developed commercially an inexpensive product that successfully interrupts the spread of viruses such as rhinovirus or influenza virus. Problems with iodine result, for example, from its toxicity, and the fact that it is an irritant for animal tissue. The action of iodine is non-selective as between bacterial and mammalian protein, and its uncontrolled use upon the skin may cause severe irritation. Further, its activity may be diminished or neutralized by the action of biological fluids such as blood serum. Efforts to modify iodine to avoid these difficulties have not been completely successful.

References exist in the literature on the bactericidal action of acids such as citric, (e.g., Reid, James D., "The Disinfectant Action of Certain Organic Acids", *American Journal of Hygiene*, 16, 540–556 (1932)). However, virucidal action is fundamentally different from bactericidal action in that viruses and bacteria represent different microorganisms with different characteristics. For instance, viruses do not replicate outside host cells whereas bacteria do. Quaternary ammonium compounds such as benzalkonium chloride are often effective against bacteria but not against viruses such as the various rhinoviruses.

Although it is known that rhinoviruses are labile to aqueous solutions of acids under low-pH conditions (e.g. Davis, B. D. et al; "Microbiology" p. 1303. Harper E. Row (Publishers) New York, 1973 and Rueckert, R. R., "Picornaviral Architecture" Comparative Virology - Academic Press New York (1971), pp. 194–306), known references do not mention the utilization of this concept in epidemiological contexts such as interruption of the chain of infection caused by rhinoviruses. To the best of our present knowledge the only systematic study of the virucidal action of organic acids (citric, malic, etc.) which exists in the generally available literature, was carried out by Poli, Biondi, Uberti, Ponti, Balsari, and Cantoni (Poli, G. et al: "Virucidal Activity of Organic Acids" *Food Chem.* (England) 4(4)251–8 (1979)). These workers found that citric, malic, pyruvic and succinic acids, among others, were effective against herpesvirus, orthomyxovirus and rhabdovirus (Rabies virus). Their experiments were carried out at room temperature with aqueous solutions of pure acids. No substrate or carrier was used. The three viruses chosen for study by these workers were all "enveloped" viruses, resembling, in that regard, parainfluenza 3. Poli et al also observed that these acids were not effective against adenovirus which, it will be recalled, is a "naked" virus. Based on this, they concluded that these acids were effective against "enveloped" viruses but not against "naked" viruses.

It is known to those skilled in the art that adenoviruses are resistant to acids.

*Archiv fur Libensmittelhygiene*, 29, 81–120 (1978) reports a strain of adenoviruses to be susceptible to certain disinfectant surface active agents in aqueous solution. There is no suggestion, however, of combining such disinfectant surface active agents with an organic acid or with a substrate or carrier.

The use of acidic solutions of anionic surfactants as sanitizers in the dairy, beverage and food processing industries is discussed in Dychdala, G. R., "Surface-Active Agents: Acid-Anionic Compounds", *Disinfection, Sterilization, and Preservation*, S. Block (ed.), 3rd edition, pages 330–333 (1983). Significantly, this reference specifically teaches that such sanitizers must be used with care and kept out of the reach of children because of their acidity. See also U.S. Pat. No. 3,969,258 and German Offenlegungsschrift No. 2,539,016. In addition, see U.S. Pat. Nos. 4,105,782 and 4,105,783 which teach that to be nonirritating, products such as shampoos, lotions, and creams should have pHs in the range of 3.5 to 7.5.

The use of anionic surfactants as bactericides is discussed in Baker et al., "The Bactericidal Action of Synthetic Detergents", *Journal of Experimental Medicine*, Vol. 74, pages 611–620 (1941); Cowles, P. B., "Alkyl Sulfates: Their Selective Bacteriostatic Action", *Yale Journal of Biology and Medicine*, Vol. 11, pages 33–38 (1938); and Newton, B. A., "Surface-Active Bactericides", *Symposium for the Society for General Microbiology*, No. 8, pages 62–93 (1958). The Baker et al. and Cowles references report that under the experimental conditions employed, anionic surfactants were found to be ineffective against Gram-negative organisms. The Newton reference (at page 67) points out that various substances, including soaps, can prevent anionic and cationic surfactants from killing bacteria. Similarly, U.S. Pat. No. 3,244,636 reports interference between detergent compositions and antimicrobial agents such that the detergent and the antimicrobial agent are each less effective when used in the presence of each other.

U.S. Pat. No. 3,650,964 discloses low foaming sanitizer compositions employing selected anionic surfactants in an acid medium. U.S. Pat. No. 3,141,821 discloses allegedly synergistic combinations of a bacteriostatic compound, such as hexachlorophene, and an acid solution of an anionic surfactant. The patent describes formulating the compositions in a pre-surgical scrub, an acn preparation, an after-shave lotion, an under-arm deodorant, a body powder, and a detergent bar. See also German Auslegeschrift No. 1,105,549 and German Offenlegungsschrift No. 2,312,280.

U.S. Pat. No. 3,408,298 to Baravalle discloses germicidal compositions which include a quaternary ammonium complex in combination with nonionic, cationic, or anionic detergents. These compositions are said to be suitable for use in preparations which come into contact with skin. Similarly, U.S. Pat. No. 3,023,144 describes a fungicide/bactericide made from d-limonene and salicylic acid which can be topically applied, and U.S. Pat. No. 3,278,370 describes soaps which include higher alkyl benzoates, such as sodium dodecylbenzoate, as bacteriostatic agents.

SUMMARY OF THE INVENTION

The present invention provides a virucidal composition, the method of use and the product thereof which are highly effective over a broad spectrum of viruses and yet can be produced and used with safety. We have discovered that when at least one or more genus of a respiratory virus is contacted with an effective amount of a virucidal composition comprising a carboxylic acid having the formula R—COOH, as explained hereinbelow in greater detail, the virus is substantially inactivated thereby interrupting and preventing the spread of the virus. These acids, which may be used in combination with a surfactant as discussed below, inactivate certain respiratory viruses, enveloped (e.g. parainfluenza) and naked (e.g. rhinovirus, poliovirus and adenovirus). A suitable carrier or substrate, such as facial tissue or a nonwoven web, incorporating such compositions is particularly useful in preventing the spread of the virus. In general, these compositions and products can be handled without difficulty and are not believed to have any harmful effects when used in accordance with the invention. The compositions have little or no deleterious effects on color, odor, strength, or other important properties of the substrate or carrier. The products, for example, may be used as a dry wipe or maintained moist and used as a wet wipe.

In certain embodiments of the invention, organic acids and anionic surfactants, e.g., malic acid and a sodium alpha-olefin sulfonate surfactant, are used as active ingredients in germicidal products which are applied directly to the skin, such as, hand-washing soaps, skin-care lotions, soapy-lotions, or wipes containing these materials. Optionally, the products can include an alcohol, such as, specially denatured ethyl alcohol, ethyl alcohol, and isopropyl alcohol as an additional active ingredient.

As demonstrated in detail below, formulations containing these active ingredients, in addition to killing viruses, also effectively kill bacteria and yeasts. In particular, the formulations have been found to kill a variety of microorganisms both in in vitro experiments performed in test tubes and, even more importantly, in in vivo experiments performed on human hands.

Moreover, notwithstanding their germicidal activity, the formulations have been found to be non-irritating to human skin. This combination of a high level of skin friendliness and germicidal aggressiveness has not existed in prior art products. The manufacturers of such prior products have been unable to find a combination of ingredients which will effectively destroy microorganisms on living skin, but not substantially irritate the skin itself. Rather, such manufacturers have made compromises such that their products have either had a high level of skin friendliness or a high level of germicidal activity, but not both.

The present invention provides compositions having these two, seemly incompatible, characteristics. It is this ability to simultaneously kill microorganisms and yet not cause substantial levels of skin irritation which makes the invention of particular value in controlling the spread of bacterial, viral and yeast infections both in the home and in clinical settings.

In addition to the foregoing characteristics, the formulations of the invention are also compatible with the constraints placed on skin care products by the marketplace. Thus, the formulations have been found to have extended shelf-lives. Similarly, the ingredients making up the formulations, including the active ingredients, are readily available at moderate cost.

DESCRIPTION OF THE PREFERRED EMBODIMENTS

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the appended claims.

The present invention results from the unexpected discovery that certain acids such as citric, malic, succinic, and benzoic, used in suitable concentrations, as further described herein, are highly efficacious against rhinoviruses 16, 1A, and 86. When used in the presence of a surfactant such as sodium dodecyl sulfate (SDS), these acids were found to be effective also against rhinoviruses 10, 13, 15, 19, 22; parainfluenza virus 1, 3, A/AICHI/2/68, B/Maryland; Herpes simplex 1 and 2; Reovirus 3; respiratory syncytial virus; and adenovirus 5. In general, the water soluble carboxylic acids useful in accordance with the invention have the following structure:

$$R-COOH$$

Wherein R may be represented by: lower alkyl; substituted lower alkyl; hydroxy lower alkyl (e.g. HOCH$_2$—); carboxy lower alkyl (e.g. HOOC—CH$_2$—CH$_2$—); carboxy, hydroxy lower alkyl (e.g., HOOCCH$_2$CHOH—); carboxy, halo lower alkyl (e.g. HOOCCH$_2$CHBr—); carboxy, dihydroxy lower alkyl (e.g. HOOC—CHOH—CHOH—); dicarboxy, hydroxy lower alkyl

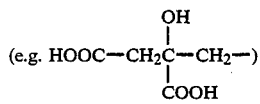

(e.g. HOOC—CH$_2$C(OH)(COOH)—CH$_2$—)

lower alkenyl, carboxy lower alkenyl (e.g. HOOCCH=CH—), dicarboxy lower alkenyl

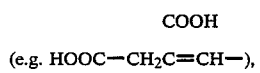

(e.g. HOOC—CH$_2$C(COOH)=CH—), phenyl (e.g. C$_6$H$_5$—); substituted phenyl (e.g. hydroxy phenyl HO—C$_6$H$_4$—). Other acid examples include hydroxy lower alkyl, lactic; carboxy, hydroxy lower alkyl, e.g. 2-methyl malic; carboxy, halo lower alkyl, e.g. 2-chloro-3-methyl succinic; carboxy, dihydroxy lower alkyl, e.g. 2-methyl tartaric; dicarboxy, hydroxy lower alkyl, 2-methyl citric acid; and carboxy lower alkenyl, e.g. fumaric. The above definitions are used in an illustrative but not a limiting sense. The term "lower" as used herein refers to an acid where "R" contains one to six carbon atoms. The term "substituted" indicates that one or more hydrogen atoms are substituted by halogen atoms (F, Cl, Br, I), hydroxyl groups, amino groups, thiol groups, nitro groups, cyano groups, etc.

The surfactant may be nonionic (e.g. the polyoxyethylenated alkylphenols such as TRITON X-100 ®, manufactured by Rohm and Haas; the polyoxyethylenated sorbitol esters such as TWEEN 40 ®, manufactured by ICI, Inc. (United States)), cationic (e.g. cetylpyridinium chloride C$_5$H$_5$N$^+$(CH$_2$)$_{15}$CH$_3$ Cl$^-$), methylbenzethonium chloride (Me$_3$CCH$_2$C(Me)$_2$C$_6$H$_3$-(Me)—OCH$_2$CH$_2$OCH$_2$CH$_2$+N(Me)$_2$CH$_2$C$_6$H$_5$ Cl$^-$) or anionic (e. g., sodium dodecyl sulfate, (CH$_3$(CH$_2$)$_{10}$—CH$_2$OSO$_3$—Na), the 1,4-bis (2-ethylhexyl) ester, sodium salt of sulfosuccinic acid, as manufactured by American Cyanamid Company under the trade name of AEROSOL OT, and alpha-olefin sulfonate salts). All three types of surfactants are generally effective for rhinoviruses. For other types of viruses, the anionic surfactants are preferred. The preferred anionic surfactants may be represented by the structures:

$$(ROSO_3)_xM^+ \text{ or } (RSO_3)_xM^+ \quad (1)$$

wherein M$^+$ is a mono, di or trivalent metal cation or an ammonium or substituted ammonium ion; x is an integer; and R is an alkyl group. As used herein, an "alkyl" group includes saturated and unsaturated hydrocarbon chains.

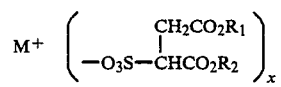

wherein, M$^+$ and x are defined as above and R$_1$ and R$_2$ may be the same or different and may be represented by straight or branched chain aliphatic groups. The above anionic surfactants are presented in an illustrative rather than a limiting sense. Surfactants, in general, are not virucidal with respect to naked viruses such as rhinovirus.

In the case of products in which the active ingredients are applied to a cellulosic web, a mixture of citric and malic acids and sodium lauryl sulfate are the preferred acids and surfactant, respectively, of the various acids and surfactants referred to above. With particular reference to facial tissues, these ingredients are preferably added to the facial tissue at add-on amounts of between about 0.5 and about 6.0 mg total acid per square inch, e.g., at add-on amounts of 5.4 mg/in$^2$ or 2.5 mg/in$^2$. For example, an addition rate of 0.5 mg/in$^2$ of malic acid (1.6% by weight) and 1.0 mg/in$^2$ of citric acid (3.2% by weight) has been found to work successfully. The addition is preferably performed using an aqueous solution of the ingredients comprising: 37.3% citric acid, 18.7% malic acid, 7.5% sodium lauryl sulfate, and 36.5% water. The aqueous solution can be conveniently applied to the facial tissue stock using, for example, a DAHLGREN® LAS (liquid application system) treater.

In the case of products which are to be applied directly to the skin, malic acid and a sodium alpha-olefin sulfonate anionic surfactant are the preferred acid and surfactant of the various acids and surfactants referred to above. Of these surfactants, those having between about 8 and about 18 carbon atoms are preferred and those having between about 12 and about 16 carbon atoms are most preferred. Also, for these types of products, an alcohol can be included in the product as an active ingredient. The preferred alcohol is ethyl alcohol. Other alcohols which can be used include isopropyl alcohol, propyl alcohol, or mixtures of ethyl and isopropyl alcohol. In general, alcohols having up to six carbon atoms can be used. Suitable ranges for these active ingredients in such skin-contacting products are as follows: acid—0.1 to 10% w/v with 2–7% being preferred; surfactant—0.1 to 10% v/v, with 0.5–7% being preferred, for lotions and 0.1 to 60% v/v, with 2–55% being preferred, for soaps; alcohol (when used) —0.5 to 10% v/v with 2–6% being preferred. Particularly preferred formulations for the products are given below in connection with the "Soap and Lotion Experiments."

Although the invention is not limited to the use of a cellulosic web (such as facial tissue, bathroom tissue, hand towels for washroom and other uses and the like) as the substrate or carrier for the virucidal agents, a facial tissue impregnated with these novel virucidal agents sufficiently illustrates the underlying principle and represents a simple and useful embodiment of the invention. For this reason, the first set of experiments described in the paragraphs which follow were carried out using facial tissues as the substrate. Examples of suitable nonwoven substrates are wet wipe materials such as wet-creped hand towels and spunbonded and meltblown polymeric webs commonly used in the production of disposable hospital items such as surgical drapes, gowns, bedsheets, pillowcases, and the like. Other examples of nonwovens include composites of natural and/or synthetic fibers, formed by turbulent admixing, in nonwoven form. Textile materials of all types, including laminates of different materials, may be used as suitable substrates. For example, hygienic face masks used by persons suffering from respiratory illnesses provide an excellent means for utilizing the present invention Other essentially inert carriers i.e., those which are essentially non-toxic and non-irritating to human or animal tissue under the conditions of normal use, will be apparent to those skilled in the art for applications such as lotions, sprays, creams, polishes and the like.

FACIAL TISSUE EXPERIMENTS

In general terms, the experimental procedure for preparing the samples used in the cellulosic web examples below was simple and straightforward. Three-ply KLEENEX® facial tissues (11 inches ×12 inches; basis weight; ca. 26 lb/2880 ft.$^2$ for all three plies combined) were impregnated with aqueous solutions of citric, malic, succinic, and benzoic acids by simple dipping. The acids were used either singly or as homogeneous mixtures. Usually the impregnating solution also contained a small percentage of a surfactant such as AEROSOL-OT [sodium salt of 1,4-bis-(2-ethylhexyl) ester of sulfosuccinic acid, manufactured by American Cyanamid], or sodium dodecyl sulfate. In certain instances, a small amount of glycerol was also used to enhance tissue softness. The saturated tissues were pressed between rolls to squeeze out excess saturant and ensure uniformity of saturation. The tissues were weighed, dried, and the degree of saturation (i.e. percent saturant pick-up) was computed. The tissues were then ready for the testing of virucidal efficacy.

The procedure adopted for testing virucidal efficacy is in accord with standard virological assay techniques (TCID$_{50}$) with simple variations necessitated by the presence of the cellulosic substrate. A description of the procedure follows.

VIRUCIDAL ASSAY PROCEDURE

I. Materials

A. Solutions

1. Neutralizing Solution
   6.4 ml 2M Na$_2$HPO$_4$
   1.2 ml 1.0M Citric Acid
   92.4 ml 1X Medium 199
   (nutrient medium
   for tissue culture)
2. Hanks' - McIlvane Salt Solution (HMSS):

| 2.0 ml 1.0M Citric Acid | Diluted to 2 liters |
   |---|---|
   | 18.0 ml 2.0M Sterile Na$_2$HPO$_4$ | with Hanks' Balanced Salt Solution |

The pH of this solution is 7.0
3. Hanks' Balanced Salt Solution:

|  | g/liter in double-distilled water |
   |---|---|
   | NaCl | 8.0 |
   | KCl | 0.4 |
   | MgSO$_4$.7H$_2$O | 0.2 |
   | CaCl$_2$ (anhydrous) | 0.14 |
   | Na$_2$HPO$_4$.2H$_2$O | 0.06 |
   | KH$_2$PO$_4$ (anhydrous) | 0.06 |
   | Glucose | 1.0 |
   | Phenol red | 0.005 |
   | NaHCO$_3$ | 0.35 |

Note:
The above solutions are not virucidal.

B. Viruses and Tissue Culture Cell Lines

1. Rhinovirus type 16, type 1A and type 86:

Rhinovirus types 16, 1A, and 86 (RV 16, 1A and 86 respectively) are grown in Ohio State HeLa (O-HeLa) tissue culture cells and stored at −60° F. until they are used. The virucidal testing involving the rhinoviruses is done using O-HeLa tissue culture test tubes incubated on a roller drum apparatus at 33° C.

2. Parainfluenza type 3:

Parainfluenza type 3 (Para 3) is grown in rhesus monkey kidney tissue culture cells and stored at −60° F. until it is used. The virucidal testing involving Para 3 virus is done using O-HeLa tissue culture test tubes incubated in a stationary position at 33° C.

3. Adenovirus type 5:

Adenovirus type 5 (Adeno 5) is grown in HEp-2 tissue culture cells and stored at 60° F. until it is used. The virucidal testing involving Adeno 5 virus is done using Human Epithelial Carcinoma—2 (HEp-2) tissue culture test tubes incubated in a stationary position at 37° C.

II. Methods

A. Virucidal Testing

A 1:1 (volume:volume) mixture of virus and saliva is prepared. A one square-inch sample is cut out of treated Kimberly-Clark KLEENEX ® tissue and placed in a plastic Petri dish. (A treated tissue is tissue impregnated with the virucidal agent under investigation.) The virus-saliva mixture (0.1 ml) is pipetted directly onto the sample and allowed to react for one minute. Note this is a two-fold virus dilution. After the reaction time of one minute, 5 ml of neutralizing solution is pipetted onto the sample in the Petri plate and agitated for 3 seconds. This is now a 100-fold virus dilution. The neutralizing solution - virus - saliva mixture is then pipetted out of the Petri plate and added to a tube containing 5 ml of Hanks' - McIlvane Salt Solution. The sample is added to the same tube by tipping the plate and using the tip of a pipette to push it into the tube. The tube containing the 10 ml of solutions and the sample is vortexed for 30 seconds. This tube contains a $10^{-2.3}$ or 1:200 dilution of virus. Ten-fold serial dilutions (fresh pipette for each dilution) are made from the $10^{-2.3}$ dilution by taking 0.3 ml of the previous dilution and adding it to 2.7 ml of Hanks' McIlvaine Salt Solution. 0.1 ml is inoculated into each tissue culture test tube. Generally two tubes are inoculated per dilution.

For each experiment two sets of controls are used. The first may be termed "the virus control" as it is designed to check the infectivity of the virus suspension itself without saliva or the tissue substrate. The virus suspension is diluted serially 10-fold in HMSS. 0.1 ml of specific dilutions are inoculated per tissue culture cell test tube. The information obtained from this control gives the number of infectious virus units that are contained in the virus solution that has been stored at −60° F. and insures that the aliquot of virus solution used in the experiment has not lost infectivity during the freezing, storage, or thawing processes.

The second control, "the tissue control", consists of performing the virucidal testing experiment using one square inch of an untreated KLEENEX ® tissue. The information obtained from this control gives the number of infectious virus units that can be recovered from an untreated one inch square wipe following the virucidal testing procedure. The inoculated tissue culture tubes are examined for seven days for evidence of viral infection.

The endpoint of a virucidal test for a given wipe is that dilution of virus which infects actually or is calculated to infect only one of the two inoculated tubes. This number is defined as tissue culture infective dose, or $TCID_{50}$. The results of the virucidal activity of a given wipe are usually given as the "log difference" between the common log of the $TCID_{50}$ result of the treated sample subtracted from the common log of the $TCID_{50}$ of the untreated sample.

The virucidal efficacy of a sample may be derived from the "log difference" in the following manner:

$$\text{Virucidal Efficacy} = \left(\frac{X - Y}{X}\right) 100\%$$

Where:

X = the initial concentration of the virus (infectious units/0.1 ml) of untreated sample used as control.

Y = the final concentration of the virus (infectious units/0.1 ml) of the treated sample.

The following examples explain the computation procedure. (In the experiments, the final virus concentration was always less than or equal to $10^{2.3}$ infectious units/0.1 ml. For the majority of the results, the final virus concentration was less than $10^{2.3}$. With an initial virus concentration of $10^{6.3}$, thus would signify a log difference greater than 4 and a "kill" of greater than 99.99%).

1. Initial Concentration: $X = 10^{6.3}$
Final Concentration: $Y = 10^{2.3}$
Log Difference = $(\log 10^{6.3} - \log 10^{2.3}) = 4$ $$\text{Virucidal Efficacy} = \left(\frac{10^{6.3} - 10^{2.3}}{10^{6.3}}\right) \times 100\%$$

$$= \left(\frac{10^{2.3} \times (10^4 - 1)}{10^{6.3}}\right) \times 100\%$$

$$= 99.99\%$$

2. Initial Concentration: $X = 10^{4.8}$
Final Concentration: $Y = 10^{2.3}$
Log Difference = 2.5

$$\text{Virucidal Efficacy} = \left(\frac{10^{4.8} - 10^{2.3}}{10^{4.8}}\right) \times 100\%$$

$$= 99.7\%$$

The procedure outlined above is in conformity with standard microbiological assay techniques. It yields reliable and reproducible results within the limits of variability associated with biological experiments.

III. Results

The results are shown in Tables I, II, and III. The data in Table I show that simple organic carboxylic acids such as citric, malic, tartaric, succinic and substituted derivatives thereof (e.g. 2-bromo- succinic), and benzoic acid and its substituted derivatives (salicylic acid), used in a facial tissue in suitable concentrations, are highly virucidal against rhinovirus 16 and parainfluenza 3.

Furthermore, the data in Table I show that, when used in conjunction with a surfactant such as Aerosol OT or sodium dodecyl sulfate, the concentrations of the acids in the facial tissue may be lowered without sacrificing virucidal efficacy.

Table II lists the results of experiments with acid mixtures chosen from the group citric, benzoic, succinic, and malic. The data show that the facial tissues treated with the acid mixtures are virucidal against rhinovirus 16 and parainfluenza 3. The data in Table II show that the facial tissue impregnated with a mixed acid system such as citric and malic and an appropriate surfactant such as SDS, is efficacious against rhinovirus 16, 1A and 86 and adenovirus 5. The combination has also been found effective against a variety of rhinoviruses including rhinoviruses 10, 13, 15, 19 and 22; parainfluenza virus 1, 3, A/AICHI/2/68, B/Maryland; Herpes simplex 1 and 2; Reovirus 3; respiratory syncytial virus, AIDS virus, and polio virus. As these examples demonstrate, in accordance with the present invention, simple organic acids such as citric/malic/succinic, when used in conjunction with a suitable surface-active agent such as SDS, are highly virucidal against common respiratory viruses of which rhinovirus 16, 1A and 86, parainfluenza 3, and adenovirus 5 are typical examples. In addition, products using facial tissues as the means of deployment of the virucidal compositions mentioned are highly effective.

The significance of the invention resides in the fact that it provides the basis for interrupting the chain of infection caused by respiratory viruses. As viruses do not replicate outside the host cell, the degree of inactivation demonstrated in the experiments offers a simple and practical means of reducing the virus concentration in the vicinity of a person infected with a respiratory virus. This, in turn, significantly reduces the potential of the infection to spread.

In order to more specifically illustrate the improved effects obtained in accordance with the invention, additional examples were carried out varying the concentration of selected acid compositions and measuring virucidal activity at one and five minutes. These results are summarized in Table IV. In general, the acid compositions within the scope of the invention are virucidally effective to a high degree, e.g., in the case of rhinoviruses or parainfluenza viruses, they produce a log drop of 2 or greater inactivation in one minute or less. For adenoviruses the time will be five minutes or less. In general, the degree of inactivation is greater after five minutes than after one minute as would be expected. Certain minor inconsistencies appear in the reported results due to the margin of error and the nature of the test procedure. It will be recognized by those skilled in this art that effectiveness is also influenced by the amount of the composition available for contact with the virus which, in turn, depends on the nature of the carrier. For example, as shown in Table IV, below, a relatively thick carrier with large voids such as wool may be ineffective unless treated with large amounts of the composition. On the other hand, a lightweight, relatively closed structure such as tissue or nonwoven material will require less of the composition. Based on the tests described, however, the effectiveness of a given combination of composition and carrier may be determined. For example, as shown in Table IV, citric acid is effective at concentrations tested from 5% to 10% add-on. The procedure used is described below.

For these examples $TCID_{50}$ results were obtained using WI-38 cells of low passage from Flow Laboratories, Inc. which were initially passed at least once to insure growth potential. The bottles were then split 1:2 and seeded in 96-well cluster tissue culture plates with a flat bottom growth area of 0.32 $cm^2$ obtained from M A Bioproducts. The cells were incubated at 37° C. in 5% $CO_2$ and, after 24 hours, were usually 80 to 90% sheeted and normal in appearance before use in the assay. The medium (2% mM) used for both dilutions and maintenance of the cells was MEM Eagles with Earles BSS (with glutamine, gentamicin sulfate and 2% fetal calf serum added). Rhinovirus 1A was obtained from the National Institute of Allergy and Infectious Diseases, Bethesda, Maryland. A vial was grown in WI-38 cells and harvested after showing 4+ cytopathogenic effect (CPE) at 2 days post inoculation. The virus was harvested, aliquoted, and frozen at −70° C. and later titered in WI-38 cells in 96-well cluster plates.

For the assay, the medium was removed from the plates by placing sterile gauze between the plate and the cover and turning the plate over. All six wells used received 0.1 ml of 2% mM. To the wells which were to be used as cell controls, another 0.1 ml of 2% mM was added. To the cells which were to receive the compounds, 0.1 ml of the appropriate dilution of material was added to each of six wells. The stock virus was mixed 1:1 with 2% mM for the initial dilution. One hundred microl. of this virus dilution were then added to a treated disc in a Petri dish. The virus was applied evenly over a tissue disc using a microliter syringe. The virus was allowed to remain on the disc for 1 minute or 5 minutes, then 5 ml of 2% mM was added to the disc in the Petri dish and the disc was slightly agitated. The disc and the solution were removed and placed in a sterile tube and agitated by vortexing for 30 seconds, representing the first dilution. Three ten-fold dilutions were made from the original tube and 0.1 ml of all four dilutions were added to the mono-layered WI-38 cells. Six wells were used for each dilution. Untreated controls were tested at 1 and 5 minutes, with and without virus and a virus titration was also run with each assay. The plates were reincubated at 37° C. in 5% $CO_2$ for the duration of the test.

Acids such as sulfamic and phosphoric were also found to be virucidal. However, these acids have been found to degrade carriers such as tissue.

Because some of the acids are soluble in water, they can be applied to many substrates from an aqueous solution with great ease either by dipping, coating, or other conventional means such as spraying or gravure printing. The composition is applied to the substrate in an amount sufficient to provide virucidal activity as defined herein. It is understood that reference to a soluble acid means that the acid is sufficiently soluble so that it will produce a virucidal effect. As will be seen from the examples above, solubilities may range from high solubility (e.g., glycolic acid used in Examples 39–41) to low solubility (e.g., salicylic acid used in Examples 11, 12, and 42–45). While the lower effective limit for the acids has not been precisely determined, in general, for a substance such as facial tissue having a basis weight in the range of 23 to 31 lbs./2880 $ft.^2$ (3 ply), there should be a pick-up of at least about 2 percent and preferably about 5 percent of acids such as citric on a dry basis. Other substrates such as nonwovens may be utilized as well.

When mixtures of acids are employed, they may be in any proportion, but preferably the mixtures contain at least about 0.2 to 10% of each acid based on the weight of the substrate after drying.

When surfactants are included, they are preferably selected from the group of anionic surfactants and included in the amount of about 0.05 to 5% based on the weight of the substrate after drying.

In the application of the virucidally active organic acids defined herein in other substrates or carriers such as lotions, mouthwash, creams, sprays, polishes and the like, the preferred members being substantially non-toxic or non-irritating upon contact with human or animal tissue, the virucidally effective amount may be determined readily upon application of the procedures set forth herein. For example, a log drop of 2 or more would mean that 99 percent or more of the host viruses are inactivated upon contact with the acid compositions described and claimed herein. These applications of the invention using carriers other than cellulosic webs will now be illustrated by the following examples in which germicidal soaps and lotions are prepared which employ organic acids, anionic surfactants, and, optionally, alcohols, as active ingredients.

LOTION EXPERIMENTS

These experiments relate to the preparation and testing of soaps and lotions containing malic acid, sodium alpha-olefin sulfonate (sold under the tradename BIO-TERGE ® AS-40 by Stepan Chemical, Northfield, Illinois), and ethyl alcohol as active ingredients.

Except where otherwise indicated, all materials used in the experiments were commercially available, standard microbiological materials, media, and chemicals.

The Minimum Inhibitory Concentration test (the "M.I.C." test; see the Official Methods of Analysis of the Association of Analytical Chemists) was used to determine the minimum concentrations of active ingredients (i.e., organic acid and surfactant) which would result in germicidal activite. Depending upon the particular experiment, the test microorganisms were exposed to the active ingredients for periods of 30 seconds, 60 seconds, or 10 minutes.

The M.I.C. test was performed generally as follows. Test microorganisms were incubated at 36° C. in 5.0 milliliters of nutrient broth (GIBCO) for 24-48 hours for more than 4 and less than 30 transfers. Cell densities were determined prior to each experiment.

A standard solution of germicide was prepared by dissolving malic acid (119 g, 0.89 mole) and BIO-TERGE ® AS-40 (59.3 g of a 40% v/v solution, 0.069 mole) in water and bringing the final volume to one liter. Thus, the concentrations of malic acid and BIO-TERGE ® in the final solution were 0.89 M and 0.069 M, respectively. Serial two-fold dilutions of this solution were made until ten solutions (i.e., undiluted, 1:2, 1:4, 1:8, etc.) were obtained. The test microorganism (0.2 ml of about $10^8$ cfu/ml) was added and mixed with 2 ml of each test solution. After the required length of exposure time (30 sec, 1 min, 10 min), a loopful (10 micoliters) of each microorganism/germicide test suspension was transferred to a neutralizing both (5 ml of Letheen broth) and the resulting mixtures were incubated at 36° C. for 24 and 48 hours. At the end of the incubation periods, the mixtures were examined for the presence or absence of growth of the microorganism. The MIC was established by determining the lowest concentration of germicide which upon exposure to the test microorganism resulted in no growth. For convenience, the concentrations of malic acid and BIO-TERGE ® in the test suspensions were taken to be the concentrations of the test solutions before the addition of a test microorganism suspension. All such concentrations are reported as μmole/ml, except for the concentrations in the undiluted final solution which are reported as mmoles/ml.

The ability of the neutralizing medium in the second set of test tubes to neutralize the effects of the active ingredients was tested as follows. Known quantities of malic acid and BIO-TERGE ® AS-40 surfactant were added to test tubes containing 5 milliliters of neutralizing medium to determine the maximum quantity of a given concentration of active ingredients which could be added to the neutralizer and still be inactivated. Representative microorganisms (i.e., a yeast and a gram-positive and a gram-negative bacterium) were used in the test. The results shown in Table VI are representative and demonstrate that Letheen broth with 0.1% v/v TRITON X-100 ® is an adequate neutralizing medium for malic acid and BIO-TERGE ® AS-40.

I. Selection of Active Ingredients

Malic acid and BIO-TERGE ® AS-40 were selected as the preferred active ingredients as follows.

Initially, using the M.I.C. test, it was determined that malic and citric acid, the acids used in Kimberly-Clark's AVERT ® virucidal tissue, need not be used together to achieve germicidal activity in aqueous solutions, but rather only one acid in combination with a surfactant is required.

Further, it was determined that exposure of microorganisms to either malic (12% w/v) or citric acid (10% w/v) alone or to a surfactant alone resulted in no significant germicidal activity against the bacteria and yeast tested. That is, a synergy was observed between the organic acid and the surfactant, in that it was found that both must be used to achieve significant germicidal activity. Among other tests which were performed in establishing this synergistic effect, malic acid solutions having pHs in the range of 2.41-3.28 were tested. Even with a 10-minute exposure time, no bactericidal activity was observed for these solutions. These results are considered surprising since organic acid are known to have some germicidal activity as a result of their low p(! (see Scarles, W. B., W. C. Frazier, J. B. Wilson, and S. G. Knight. 1956. *Microbiology*. 2nd Ed. Harper Brothers, New York, NY., page 101.)

An investigation was then made to determine the effect of pH on the germicidal activity of the combination of an organic acid and a surfactant. In these experiments, the pH of the test solutions was adjusted, using 1.0 N HCl or NaOH, to values of 2.0, 3.0, 3.5, 4.0, and 5.0. Germicidal activity against *Staphylococcus aureus* was noted at pH 2.0 for a ten minute exposure time. This level of activity did not significantly decrease at pHs of 3.0, 3.5 and 4.0. At pH 5, however, a reduced activity was detected. From these data, it was concluded that germicidal activity was primarily dependent on the concentrations of acid and surfactant and secondarily dependent on the hydrogen ion concentration.

A series of experiments was then conducted using the M.I.C. methodology to determine which of a variety of surfactants and organic acids would result in maximum germicidal activity.

The surfactants tested (in combination with malic acid) were as follows:
AEROSOL OT (sulfosuccinate)
BIOSOFT D-35X (salt of dodecyl benzene sulfonate)
BIOSOFT N-300 (salt of dodecyl benzene sulfonate)
BIO-TERGE ® AS-40 (sodium alpha-olefin sulfonate)
FIZUL 10-127 (sulfosuccinate)
IGEPAL CO 620 (nonionic)
IGEPAL CO 630 (nonionic)
MAPROFIX (anionic)
NEODOL 25-3 (nonionic)
NEODOL 25-3S alkyl sulfate)
NEODOL 25-9 (nonionic)
NEODOL 91-2.5 (nonionic)

NEODOL 91-6 (nonionic)
NONOXINOL-9 (nonionic)
OCTOXYNOL-7 (nonionic)
PARETH-91-3 (nonionic)
PARETH-91-6 (nonionic)
PARETH-25-3 (nonionic)
PARETH-25-6 (nonionic)
PARETH-15-12 [nonionic)
SDS (alkyl sulfate)
SIPEX BOS (alkyl sulfate)
SIPEX CAV (alkyl sulfate)
STEOL CS-230 (alkyl sulfate)
STEPANOL WAT (alkyl sulfate)
SURFINE AZI-A (anionic)
SURFINE WLL (anionic)
TAURANOL WSP (taurate salt)
TERGITOL 15-S-12 (nonionic)

The acids tested (in combination with BIO-TERGE ® AS-40) were as follows:
Aspartic Acid
Caprylic Acid
Citric Acid
Glutamic Acid
Glutaric Acid
Glycolic Acid
Lactic Acid
Malic Acid
Pelargonic Acid
Pyruvic Acid
Valeric Acid The test organisms used for the surfactant tests were *Staphpylococcus aureus* 6538 and *E. coli* 25922; the test organism for the acid tests was *Staphylococcus aureus* 6538.

The following surfactants were found to be most effective:
SDS
BIO-TERGE ® AS-40
AEROSOL OT
STEOL CS-230
STEPANOL WAT
BIOSOFT N-300
BIOSOFT D-35X
MAPROFIX
NEODOL 25-3S
SIPEX CAV Less effective were:
TAURANOL WSP
FIZUL 10-127
NEODOL 91-2.5

Essentially ineffective were:
SURFINE AZI-A
SURFINE WLL
IGEPAL CO 630
IGEPAL CO 620
NEODOL 91-6
NEODOL 25-3
NEODOL 25-9
SIPEX BOS
TERGITOL 15-S-12
NONOXYNOL-9
OCTOXYNOL-7
PARETH-91-3 (slightly effective)
PARETH-91-6
PARETH-25-3
PARETH-25-6
PARETH-15-12

As to the acids, in addition to malic acid, the following acids were found to be effective:
Valeric Acid
Lactic Acid
Glycolic Acid
Pelargonic Acid
Aspartic Acid
Citric Acid Less effective, but still active were:
Pyruvic Acid
Glutaric Acid
Glutamic Acid
Caprylic Acid In addition to the foregoing, a series of virology tests were performed. These tests revealed that the following surfactants, when combined with a citric acid/malic acid mixture, were effective against Rhino virus 16:
SDS
BIO-TERGE ® AS-40
AEROSOL OT
BIOSOFT D-35X These surfactants were also effective against Para-2 virus, even when used without an organic acid. However, the surfactants were not effective against Rhino-16 when used alone.

The virology tests further established that SDS and BIO-TERGE ® AS-40, when combined with a citric acid/malic acid mixture, were effective against: Adeno-5 and Reovirus, while AEROSOL OT, BIOSOFT D35X, and BIOSOFT N-300 were ineffective. SDS was also found to be effective against Adeno-5 when used alone, but not against Reovirus. C BIO-TERGE ® AS-40 by itself was ineffective against both of these viruses.

With regard to the acids, the virology tests showed similar effectiveness for all of the acids when used in combination with the surfactant, provided the moles of free acid were kept constant.

From the foregoing, it was concluded that the combination of an anionic surfactant with malic acid in general produced an effective germicide, while the combination of a nonionic surfactant with malic acid was generally ineffective. Of the anionic surfactants, all of the alkyl sulfates, except SIPEX BOS, were effective. However, these surfactants are prone to hydrolysis in acidic aqueous solutions, and thus are not well-suited for use in the preparation of liquid soaps and lotions. In particular, SDS, which in combination with malic acid was found to be a highly effective germicide, suffers from this hydrolysis problem and becomes ineffective with time.

The alkyl sulfonates, on the other hand, were found to be effective against both bacteria and viruses and are stable in acidic aqueous solutions. In particular, of the many surfactants tested, none was found to be more effective, on an equimolar basis, than BIO-TERGE ® AS-40 in producing germicidal activity while retaining stability in an acid solution.

With respect to acids, on an equal molar basis, citric acid and malic acid were equally or more effective than the other organic acids tested. A subjective selection between these two acids was made by incorporating each of the acids into lotion and soap formulations containing BIO-TERGE ® AS-40 and applying the formulations to skin. Less stinging was found with emulsions containing malic acid than with emulsions containing citric acid. Accordingly, the malic acid/BIO-TERGE ® AS-40 combination was considered the preferred acid/surfactant combination for use in soap and lotion formulations.

II. In Vitro Testing of the Active Ingredients

The M.I.C. method (10 minute exposure time) was employed to evaluate the effectiveness of the malic acid/BIO-TERGE® AS-40 combination against a series of microorganisms. Specifically, the active ingredients were tested against 23 microorganisms recommended by the FDA for the testing of germicidal products (see Federal Register, Dept. of Health, Education, and Welfare, FDA-OTC Topical Antimicrobial Products, Part II, 1978. Vol. 43, No. 4:1210-1249.)

The microorganisms tested and the minimum inhibitory concentrations found effective against the microorganisms are set forth in Table VII As shown therein, the preferred active ingredients are germicidal against representative groups of both gram-positive and gram-negative bacteria, as well as against yeasts. Moreover, even when the exposure time was reduced from 10 minutes to either 60 or 30 seconds, the malic acid/BIO-TERGE® AS-40 combination retained germicidal activity against all microorganisms tested.

Because bacterial susceptibility to germicidal agents can change with the age of a culture (see Scarles, supra), the active ingredients were tested against young (24-hour) and old (72-hour) cultures. No significant difference in activity was detected between young and old cultures of microorganisms of the same species.

Because microorganisms of different species sometimes "protect" each other from coming into physical contact with a given germicidal agent (see Scarles, supra), the malic acid/BIO-TERGE® AS-40 combination was tested against mixed bacterial cultures which included *Staphylococcus aureus, Staphylococcus epidermidis, Salmonella cholerasuis, Escherichia coli, Klebsiella pneumoniae, Streptococcus pyogenes,* and *Enterobacter agglomerans.* The M.I.C. methodology with a 10-minute exposure time was employed. The test showed that mixed cultures did not protect individual cells of different species from being killed by the active ingredients.

Since many species of microorganisms (e.g., *Serratia marcescens, Providencia stuartii, Pseudomonas aeruginosa, Pseudomonas cepacia, Staphylococcus aureus, Staphylococcus epidermidis,* and *Escherichia coli*) are known to acquire resistance to germicidal products (see Sobel, J. D., N. Hashman, G. Reinherz, and D. Merzbach 1982 "Nosocomial *Pseudomonas cepacia* infection associated with chlorhexidine contamination," *Am. J. Med.,* vol. 73, pages 185–186 (1982); Fox, J. G., C. M. Beaucage, C. A. Folta, and G. W. Thornton. 1981. "Nosocomial transmission of *Serratia marcescens* in a veterinary hospital due to contamination by benzalkonium chloride", *J. of Clin. Microbiol.,* 14:157–160; McBride, M. E. 1984. "Microbial Flora of in-use soap products", *Appl. and Environ. Microbiol.,* 48:338–341; and Marrie, T. J. and J. W. Costerton. 1981. "Prolonged survival of *Serratia marcescens* in chlorhexidine", *Appl. and Environ. Microbiol.,* 42:1–93–1102) experiments were performed to determine whether bacterial resistance to malic acid/BIO-TERGE® AS-40 solutions could be induced under controlled in vitro conditions.

M.I.C. testing methodology was again employed in the execution of these experiments. Specifically, the microorganisms were exposed for 10 minutes to serial dilutions of malic acid/BIO-TERGE® AS-40, both in aqueous solution and in a lotion formulation (see Table VIII), and subsequently subcultured to neutralizing medium After 48 hours of incubation at 36° C., the tube exposed to the highest concentration of germicide yet showing growth was used as the inoculum for the next series of M.I.C. tests. The entire process was repeated 10 times.

The microorganisms tested were as follows:

| | |
|---|---|
| *Escherichia coli* | ATCC No. 25922 |
| *Providencia stuartii* | ATCC No. 29914 |
| *Pseudomonas aeruginosa* | ATCC No. 15442 |
| *Pseudomonas cepacia* | ATCC No. 17765 |
| *Serratia marcescens* | ATCC No. 13880 |
| *Staphylococcus aureus* | ATCC No. 6538 |
| *Staphylococcus epidermedis* | ATCC No. 12228 |

None of these microorganisms were found to have developed resistance to the active ingredients as a result of being exposed to 11 sublethal doses of the ingredients.

Based on the foregoing, it was concluded that the malic acid/BIO-TERGE® AS-40 combination was effective against a wide variety of microorganisms, was effective against both young and old microorganisms, was effective against mixtures of microorganisms, and was not likely to induce bacterial resistance.

III. Lotion Formulation

A preferred lotion formulation employing malic acid and BIO-TERGE® AS-40 as active ingredients is set forth in Table VIII.

This formulation was prepared by heating distilled water to 65° C. and then adding and dissolving each of the ingredients listed in Table VIII in the order given. After all the ingredients had dissolved, the mixture was slowly allowed to cool with stirring for 15–30 minutes. The formulation was then poured into a container and allowed to stabilize for 24 hours prior to testing.

The concentrations of active ingredients set forth in the formulation of Table VIII were selected as follows. First, concentrations of malic acid and BIO-TERGE® AS-40 of five times the M.I.C. values determined from the in vitro studies for a 30-second exposure time were employed (see Davis, B. D., R. Dulbecco, H. N. Eisen, and H. S. Ginsberg. 1980. *Microbiology,* 3rd Ed. Harper and Row, Philadelphia, PA., page 1268.) In particular, 165 $\mu$mol/ml of malic acid and 21.2 $\mu$mol/ml BIO-TERGE® AS-40 were incorporated into the lotion.

This level of active ingredients was found to be germicidal in in vitro studies However, upon initiation of preliminary in vivo studies (see below), it was found that the lotion resulted in only approximately a 1.0 log reduction of bacteria (*Serratia marcescens*) on human skin.

Higher levels of active ingredients were therefore tested. Specifically, lotions were prepared which contained concentrations of malic acid and BIO-TERGE® AS-40 which were ten times the in vitro M.I.C. values. Lotions were also prepared which contained the maximum concentrations of actives for which a stable emulsion could be prepared.

Using three representative microorganisms (*Candida albicans, Staphylocoqcus aureus,* and *Serratia marcescens*), these high concentration formulations were shown to have in vitro germicidal activity (see Tables IX and X). In particular, the higher concentrations of actives were shown to exhibit greater antimicrobial activity than lower concentrations. However, the emollients in the formulations were found to reduce the germicidal activity of the active ingredients in comparison to the level of activity seen when the ingredients were dissolved in aqueous solution.

In addition to the studies shown in Tables IX and X, quantitative in vitro tests were performed to further establish the germicidal activity of the preferred formulation of Table VIII. The quantitative tests showed that the germicidal lotion resulted in the complete kill of both *Staphylococcus aureus* and *Serratia marcescens* after as little as a 30-second exposure Similarly, challenge testing of the germicidal lotion by inoculation with microorganisms (i.e., *Escherichia coli, Pseudomonas cepacia, Serratia marcescens, Staphylococcus aureus,* and Staphylococcus epidermidis) known to show resistance in antimicrobial products resulted in no recovery of the microorganisms inoculated into the lotion formulation.

IV. Soap Formulation

A preferred soap formulation employing malic acid and BIO-TERGE ® AS-40 as active ingredients is set forth in Table XI.

This formulation was prepared in the same manner as the lotion formulation, i.e., it was prepared by dissolving each of the ingredients listed in Table XI, in the order given, in distilled water, cooling the mixture with stirring, and stabilizing the mixture for 24 hours before testing.

The level of active ingredients used in the soap formulation set forth in Table XI was based on the studies performed on the lotion formulation. Specifically, since a level of actives on the order of ten times the M.I.C. values was found to be preferred for the lotion formulation, a similar level was used for the soap formulation.

The in vitro efficacy of the soap formulation against *Candida albicans, Staphylococcus marcescens,* and *Staphylococcus aureus* was demonstrated using the M.I.C. methodology. The results are shown in Table XII. As shown in this table, the germicidal soap formulation was effective against each of these representative microorganisms.

V. Stability

Stability studies were carried out for both the germicidal soap and lotion as follows.

The products were prepared as described above and 100-ml quantities were poured into duplicate glass and polyethylene round jars. After the 24-hour stabilization period, individual jars were subjected to one of the following test conditions: three sequential seven-day, freeze-thaw cycles; five months at room temperature; three months at 37° C.; or two weeks at 50° C. The Cosmetics, Toiletries and Fragrance Association's guidelines for two-year shelf-life stability were followed in conducting these tests. The samples were monitored on a daily basis during the first three weeks of the tests and weekly thereafter.

Neither the soap nor the lotion product exhibited any separation under any of the test conditions, thus establishing that the products are physically stable. In addition, the formulations were periodically evaluated for any reduction in antimicrobial activity. No reduction was seen, thus establishing that the activity of the products is also stable under adverse storage conditions.

Additional stability studies were executed employing temperature fluctuation and motion. Again, no physical instability in the formulations was observed.

VI. Safety

Since all of the ingredients employed in both the lotion and soap products are generally recognized as safe, only Draize eye and skin irritation studies on rabbits were conducted. Specifically, 0.5 milliliters of each product were added to rabbit skin and 0.1 milliliter was added to rabbit eye. The resultant irritation was graded on a primary skin irritation scale of 0–6.0 (see Draize, J. H., G. Woodard and H. O. Calvery. 1944. "Methods for the study of irritation and toxicity of substances applied topically to the skin and mucous membranes", *Journal of Pharmacology and Experimental Therapeutics,* 82:377–390.)

The germicidal soap produced mild irritation (2.84 rating). The germicidal lotion in the lower range of concentration of actives without HAMPOSYL ® L-30 and ethyl alcohol was minimal in irritation (0.50 rating), while lotions with the maximum amount of actives with the HAMPOSYL ® and ethyl-alcohol were found to have mild to moderate irritation (2.25–3.50 ratings). Based on these tests, it was concluded that both the soap and lotion products were safe for use on human skin.

VII. In Vivo Testing

The following experiments relate to the in vivo testing of the germicidal activity of the soap and lotion products. Also included are comparison tests with existing commercial products said to have germicidal activity.

The procedures used in these tests were as follows. (See Aly, R. and H. I. Maibach. 1980. "A comparison of the antimicrobial effect of 0.5% chlorhexidine (HIBISTAT ®) and 70% isopropyl-alcohol on hands contaminated with *Serratia marcescens*", *Clin. and Experi. Derm.,* 5:197–201.)

Baseline (Resident) Test (1) Subject washes hands with bland soap and dries hands.
(2) Subject places hands into gloves.
(3) 100 ml Letheen broth +0.1% v/v Triton X-100 are poured into gloves.
(4) Subject massages fluid on hands for 60 seconds.
(5) Subject withdraws hands and dries hands with paper towel.
(6) 1.0 ml of fluid is removed from each glove. 2-fold serial dilutions of the fluid are made and are spread on nutrient agar plates for plate count.

Baseline (Transient) Test (1) Subject washes hands with bland soap and dries hands.
(2) 1.0 ml of the test organism (*Serratia marcescens,* ca. $3 \times 10^8$ cfu/ml) in nutrient broth is placed on the subject's cupped hands.
(3) Subject spreads the 1.0 ml on hands over a basin containing a disinfectant (AMPHYL) to prevent spreading of the test microorganisms.
(4) Subject allows hands to dry for 60 seconds.
(5) Subject places hands into gloves.
(6) 100 ml Letheen broth +0.1% v/v Triton X-100 are poured into gloves.
(7) Subject massages fluid on hands for 60 seconds.
(8) Subject withdraws hands and dries hands with paper towel.

(9) 1.0 ml of fluid is removed from each glove. 2-fold serial dilutions of the fluid are made and are spread on nutrient agar plates for plate count.

Soap/Lotion (Transient) Test (1) Subject washes with bland soap and dries hands.
(2) 1.0 ml of the test organism (*Serratia marcescens*, ca. $3 \times 10^8$ cfu/ml) in nutrient broth is placed on the subject's cupped hands.
(3) Subject spreads the 1.0 ml on hands over a basin with a disinfectant (AMPHYL) to prevent spreading of the test microorganisms.
(4) Subject allows hands to dry for 60 seconds.
(5) 2 grams of lotion or soap are applied to the subject's hands (3 pumps from a dispensing bottle, each pump expelling 0.7 grams of soap or lotion).
(6) Subject spreads 2 grams evenly on hands for 60 seconds.
(7) Subject places hands into gloves.
(8) 100 ml Letheen broth +0.1% v/v Triton X-100 are poured into gloves.
(9) Subject massages fluid on hands for 60 seconds.
(10) Subject withdraws hands and dries hands with paper towel.
(11) Steps 2-10 are repeated sequentially 4 additional times.
(12) 1.0 ml of fluid is removed from each glove and added to 19.0 ml of sterile saline. The resulting 20.0 ml is 2-fold serially diluted and spread on nutrient agar plates for plate count.
(13) Subject washes hands with HIBICLENS ®.

A. Lotion Tests

The initial in vivo tests on the lotion formulation were performed using a malic acid concentration of 2.22% (w/v) and a BIO-TERGE ® AS-40 concentration of 0.73% (v/v), i.e., the initial experiments were performed using concentrations of the active ingredients of five times the M.I.C. values determined for the active ingredients from the in vitro experiments. In addition to the complete lotion, tests were also performed using the lotion without actives and using the HIBICLENS ® product as controls. The concentration of *Serratia marcescens* applied to the subject's hands was approximately $10^8$ cfu/ml.

The results presented in Table XIII show a 1.25 log reduction for the lotion with actives, a 0.49 log reduction for the lotion without actives, and a 2.63 log reduction for the HIBICLENS ® product (A 1.0 log reduction represents a 10-fold (90%) reduction in the number of bacteria originally applied to the subject's skin.)

To obtain a greater log reduction, two lotions containing higher concentrations of the active ingredients were prepared (hereinafter "lotion 1" and "lotion 2"). In lotion 1, the concentrations of actives were increased to the maximum concentrations which could be added to the formulation while still retaining stability. Specifically, 5.0% w/v malic acid and 5.0% v/v BIO-TERGE ® AS-40 were used, along with 10% v/v HAMPOSYL ® L-30, 4% v/v denatured ethyl alcohol, and the other ingredients listed in Table VIII. In lotion 2, ten times the M.I.C. values were used. The concentrations of malic acid and BIO-TERGE ® AS-40 were 4.44% w/v and 2.0% v/v, respectively. Also, 10.0% HAMPOSYL ® L-30 v/v, 4.0% v/v denatured ethyl alcohol and the other ingredients listed in Table VIII were used in this lotion.

The results of the experiments using lotions 1 and 2 are shown in Table XIV. As shown therein, increasing the concentration of active ingredients resulted in a parallel increase in germicidal activity. Statistically, it was found that at both the 95 and 99% confidence intervals there was no significant difference in germicidal activity between lotion 1 and the HIBICLENS ® product. Further, it was found that at the 95% confidence interval there was no significant difference in germicidal activity between lotion 2 and HIBICLENS ®. These results are considered surprising in that HIBICLENS ®, a soap, does not contain high concentrations of emollients which can protect bacteria from attack by a germicide, while both lotions 1 and 2 are emulsified products which contain significant concentrations of emollients.

Lotions 1 and 2 were also compared to commercial lotions said to have antimicrobial activity. Specifically, Dexide Bacterial Lotion (Dexide, Inc.), Accent Plus-One (Huntington Laboratories), and EPICARE ® Antimicrobial Gel (Airwick Industries) were used in these tests. Initial testing of the Dexide product revealed that it contained a viable gram-negative microorganism (a Pseudomonas species). Accordingly, further testing of this product was not conducted.

The other two products and lotions 1 and 2 were subjected to the in vivo test protocol described above. The results are shown in Table XV. As shown therein, lotions 1 and 2 and the EPICARE ® gel were comparably effective. With regard to the Accent Plus-One product, on the other hand, lotions 1 and 2 were significantly more effective In terms of product similarity, the Accent Plus-One product is a lotion, like lotions 1 and 2, while the EPICARE ® product is a gel. Accordingly, the comparison with Accent Plus-One is considered more indicative of the efficacy of the products of the current invention, than the comparison with the EPICARE ® product.

A statistical analysis of the in vivo data for the Accent Plus-One product, the HIBICLENS ® product, lotion 1, and the vehicle for lotion 1 was performed. The analysis showed that Accent Plus-One statistically groups together with the vehicle for lotion 1, while lotion 1 (with actives) statistically groups together with the HIBICLENS ® soap.

These results are especially significant in view of the fact that HIBICLENS ® is a soap, not a lotion.

As indicated in Table VIII, HAMPOSYL ® L-30 and ethyl alcohol, both of which are used in lotions 1 and 2, are optional ingredients. HAMPOSYL ® L-30 is a surfactant having optimum fungicidal activity against *Trichophyton mentagrophytes* (Athlete's foot fungus) at lower pH levels (see Hart, J. R., "Sarcosinate surfactants in skin cleansers", *Cosmetic Tech*, January, 1980.) With regard to the ethyl alcohol, using the in vivo protocol described above, it has been found that the log reduction for lotion 1 with alcohol is 2.3 (see Table XV), while the log reduction for the same formulation minus alcohol is 1.5. The alcohol thus produces over a one-half log increase in germicidal activity. For comparison, the log reduction observed for the vehicle of lotion 1, without active ingredients, was 0.3.

B. Soap Tests

In vivo testing of the soap formulation of Table XI was also performed. Specifically, the soap formulation of the present invention was compared with a soft soap (no antimicrobial ingredients) and with the HIBICLENS® product.

As shown in Table XVI, the log reductions of the soft soap, the formulation of the present invention, and the HIBICLENS® product were 0.20, 2.25, and 2.81, respectively. Statistical analysis of this data showed that there was no significant difference between the product of the present invention and the HIBICLENS® product. The HIBICLENS® product, however, has been associated with such problems as dryness, irritation, and staining of clothing, none of which are believed to be associated with the product of the present invention.

In view of the foregoing, it is apparent that there has been provided, in accordance with the invention, virucidal and germicidal products which, under conditions of normal use fully satisfy the objectives and advantages as set forth in the previous paragraphs. In particular, germicidal soaps and lotions have been provided which kill viruses, bacteria, and yeast, which are fast acting, relatively non-irritating, odorless, colorless, and non-staining, and which are as effective or more effective than existing commercial germicidal soaps and lotions.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations which fall within the spirit and broad scope of the appended claims.

TABLE I

VIRUCIDAL EFFICACY OF SINGLE ACIDS AGAINST RHINOVIRUS 16 AND PARAINFLUENZA 3 VIRUS (EXPOSURE TIME OF ONE MINUTE)

| Example No. | Virucidal Composition[a] | Surfactant[a] | Virucidal Efficacy Rhinovirus 16 | Parainfluenza 3 |
|---|---|---|---|---|
| 1 | Citric Acid (23.2) | None | >99.99% | >99.7% |
| 2 | Citric Acid (18.7) | None | >99.99% | |
| 3 | Citric Acid (9.7) | AOT[b] (1), SDS[c] (1) | 99.99% | |
| 4 | Citric Acid (9.4) | SDS (1) | >99.99% | >99.99% |
| 5 | Succinic Acid (20) | None | >99.99% | |
| 6 | Succinic Acid (9.1) | SDS (2) | >99.99% | >99.99% |
| 7 | 2-Bromosuccinic Acid (10.4) | SDS (1) | >99.99% | |
| 8 | Malic Acid (9.4) | AOT (0.5) | 99.99% | >99.99% |
| 9 | Tartaric Acid (15) | None | >99.99% | |
| 10 | Benzoic Acid (30) | None | >99.99% | |
| 11 | Salicylic Acid (18) | None | >99.99% | |
| 12 | Salicylic Acid (9) | None | >99.99% | |

[a]The numbers in parentheses represent percent chemical used based on the weight of the facial tissue.
[b]AEROSOL OT®, the sodium salt of the 1,4-bis(2-ethylhexyl)ester of sulfosuccinic acid.
[c]Sodium dodecyl sulfate.

TABLE II

VIRUCIDAL EFFICACY OF MIXED ACIDS AGAINST RHINOVIRUS 16 AND PARAINFLUENZA 3 VIRUS (EXPOSURE TIME OF ONE MINUTE)

| Example No. | Acids in Virucidal Composition[a] | | | | Surfactant[b] | Virucidal Efficacy | |
|---|---|---|---|---|---|---|---|
| | Citric | Benzoic | Malic | Succinic | | Rhinovirus 16 | Parainfluenza 3 |
| 13 | 10.7 | 0.2 | — | — | AOT[c] (1) | >99.99% | 99.97% |
| 14 | 10.3 | 0.2 | — | — | AOT (1) | >99.99% | >99.97% |
| 15 | 10.1 | 0.2 | — | — | AOT (1) | >99.99% | >99.97% |
| 16 | 7.1 | 0.2 | — | — | AOT (1) | >99.99% | >99.99% |
| 17 | 8.0 | 0.2 | — | — | AOT (1) | >99.99% | >99.99% |
| 18 | 10.3 | — | — | 5.2 | AOT (1) | >99.99% | >99.97% |
| 19 | 10.0 | — | — | 5.0 | AOT (1) | >99.99% | >99.97% |
| 20 | 10.0 | — | — | 5.0 | AOT (1) | >99.99% | >99.97% |
| 21 | 10.4 | — | 5.2 | — | AOT (1) | >99.99% | >99.99% |
| 22 | 10.5 | — | 5.3 | — | AOT (1) | >99.99% | >99.97% |
| 23 | 10.3 | — | 5.2 | — | AOT (1) | >99.99% | >99.97% |
| 24 | 10.2 | — | 5.1 | — | AOT (1) | >99.99% | >99.97% |
| 25 | 11.1 | — | 5.6 | — | AOT (0.5) | >99.99% | >99.7% |
| 26 | 10.6 | — | 5.3 | — | AOT (1) | >99.99% | >99.7% |
| 27 | 11.1 | — | 5.6 | — | AOT (0.5) | >99.99% | >99.7% |
| 28 | 10.6 | — | 5.3 | — | AOT (1) | >99.99% | >99.70% |
| 29 | 4.8 | — | 4.8 | — | AOT (1) | >99.99% | >99.99% |
| 30 | 13.8 | — | — | 5.0 | TX 100[d] (2) | >99.99% | >99.99% |
| 31 | 5.7 | — | 5.7 | — | SDS[e] (2) | >99.97% | >99.90% |
| 32 | — | 0.2 | 9.7 | — | SDS (2) | 99.97% | >99.90% |

[a]The numbers represent percent chemical used based on the weight of the facial tissue.
[b]The numbers in parentheses represent percent chemical used based on the weight of the facial tissue.
[c]AEROSOL OT®.
[d]TRITON X-100®.
[e]Sodium dodecyl sulfate.

TABLE III

VIRUCIDAL EFFICACY OF MIXED ACIDS AND SDS AGAINST RHINOVIRUS 16, RHINOVIRUS 1A, RHINOVIRUS 86, AND ADENOVIRUS 5 (EXPOSURE TIME OF ONE MINUTE)

| Example No. | Virucidal Composition[a] | | | Virucidal Efficacy | | | |
|---|---|---|---|---|---|---|---|
| | Citric Acid | Malic Acid | Surfactant SDS[b] | RV 16 | RV 1A | RV 86 | AV 5 |
| 33 | 10.0 | 5.5 | 2.2 | >99.99% | — | — | 99.90% |
| 34 | 11.2 | 5.7 | 2.3 | >99.99% | — | — | 99.90% |
| 35 | 11.4 | 5.0 | 2.3 | >99.99% | — | — | 99.70% |
| 36 | 10.0 | 5.5 | 2.2 | >99.99% | — | — | 99.99% |
| 37 | 11.2 | 5.7 | 2.3 | >99.99% | — | — | 99.99% |
| 38 | 10.0 | 5.0 | 2.0 | >99.99% | >99.99% | >99.99% | 99.90 |

[a]The numbers represent percent chemical used based on the weight of the facial tissue.
[b]Sodium dodecyl sulfate.

TABLE IV

VIRUCIDAL EFFICACY OF SINGLE AND MIXED ACIDS AGAINST RHINOVIRUS 1A AS SHOWN BY TISSUE CULTURE INFECTIVE DOSE STUDIES

| Example No. | Acid | % Acid Add-on | One Min. Results | | Five Min. Results | | Virucidal Efficacy (% Inactivation) | |
|---|---|---|---|---|---|---|---|---|
| | | | Log Value Treated Tissue | Log Drop | Log Value Treated Tissue | Log Drop | One Min. | Five Min. |
| 39 | Glycolic | 12 | <2.0 | >3.25 | <2 | >2.75 | >99.94 | >99.82 |
| 40 | Glycolic | 9 | <2.0 | >3.25 | <2 | >2.75 | >99.94 | >99.82 |
| 41 | Glycolic | 2.4 | <2.0 | >3.25 | <2 | >2.75 | >99.94 | >99.82 |
| 42 | Salicylic | 7.2 | <2.0 | >2.33 | <2 | >2.75 | >99.5 | >99.8 |
| 43 | Salicylic | 5.4 | <2.0 | >2.33 | <2 | >2.75 | >99.5 | >99.8 |
| 44 | Salicylic | 3.6 | ≧5.17 | 0 | 4.67 | 0.5 | 0 | 68 |
| 45 | Salicylic | 1.4 | ≧5.25 | 0 | ≧5.4 | 0 | 0 | 0 |
| 46 | Succinic | 9.2 | <2.0 | >3.25 | <2 | >2.75 | >99.94 | >99.82 |
| 47 | Succinic | 6.9 | <2.0 | >3.25 | <2 | >2.75 | >99.94 | >99.82 |
| 48 | Succinic | 4.6 | <2.0 | >3.0 | <2 | >3.17 | >99.9 | >99.93 |
| 49 | Succinic | 1.8 | 3.9 | 0.8 | 3.9 | 0.4 | 84 | 60 |
| 50 | Malic | 10.5 | <2.0 | >3.25 | <2.0 | >2.75 | >99.94 | >99.82 |
| 51 | Malic | 7.9 | NA[a] | NA | <2.0 | >2.75 | NA | >99.82 |
| 52 | Malic | 5.2 | <2.0 | >3.25 | <2.0 | >2.75 | >99.94 | >99.82 |
| 53 | Malic | 2.1 | 2.38 | 2.87 | <2.0 | >2.75 | 99.9 | >99.82 |
| 54 | 2-Bromo-succinic | 2.0 | 3.33 | 1.92 | <2.0 | >2.75 | 98.8 | >99.8 |
| 55 | 2-Bromo-succinic | 10.2[b] | 2.5 | 2.5 | 2.5 | 2.67 | 99.7 | 99.8 |
| 56 | Tartaric | 11.7 | <2.0 | >3.25 | <2.0 | >2.75 | >99.94 | >99.82 |
| 57 | Tartaric | 8.8 | <2.0 | >3.25 | <2.0 | >2.75 | >99.94 | >99.82 |
| 58 | Tartaric | 5.9 | <2.0 | >3.25 | <2.0 | >2.75 | >99.94 | >99.82 |
| 59 | Tartaric | 2.3 | <2.0 | >3.25 | <2.0 | >2.75 | >99.94 | >99.82 |
| 60 | Maleic | 6.8 | <2.0 | >3.25 | —[c] | —[c] | >99.94 | [c] |
| 61 | Maleic | 4.5 | <2.0 | >3.25 | ≦2.0 | ≧2.75 | >99.94 | ≧99.8 |
| 62 | Maleic | 1.8 | 2.25 | ≧3.00 | <2.0 | >2.75 | >99.9 | >99.8 |
| 63 | Aconitic | 9.0 | <2.0 | >3.25 | <2.0 | >2.40 | >99.94 | >99.6 |
| 64 | Aconitic | 6.8 | ≦2.0 | ≧3.25 | <2.0 | >2.75 | ≧99.94 | >99.8 |
| 65 | Aconitic | 1.8 | 3.40 | 1.85 | 3.50 | 1.25 | 98.6 | 94 |
| 66 | Citric | 10.0 | <2.0 | >3.25 | <2.0 | >2.75 | >99.94 | >99.8 |
| 67 | Citric | 7.5 | ≦2.0 | >3.25 | <2.0 | >2.40 | ≧99.94 | >99.6 |
| 68 | Citric | 5.0 | ≦2.0 | ≧3.25 | ≦2.0 | >2.75 | ≧99.94 | >99.8 |
| 69 | Citric | 2.0 | 3.75 | 1.0 | <2.0 | >2.4 | 90 | >99.6 |
| 70 | Phosphoric | 5.0 | <2.0 | >3.0 | <2.0 | >3.17 | >99.9 | >99.93 |
| 71 | Phosphoric | 3.8 | ≦2.0 | ≧3.0 | <2.0 | >3.17 | ≧99.9 | >99.93 |
| 72 | Phosphoric | 2.5 | ≦2.0 | ≧3.0 | <2.0 | >3.17 | >99.9 | >99.93 |
| 73 | Phosphoric | 1.0 | 4.25 | 0.75 | 4.40 | 0.77 | 82 | 83 |
| 74 | Citric Malic | 10.0 5.0 | <2.0 | >1.75 | <3.0 | >1.40 | >98.2 | >96 |
| 75 | Citric Malic | 10.0 5.0 | <2.0 | >3.0 | <2.0 | >3.17 | >99.9 | >99.93 |
| 76 | Wool[d,e] | — | 4.6 | 0.4 | NA | NA | 60.0 | NA |
| 77 | MB PP[e,f] | — | —[c] | —[c] | <3.0 | 1.6 | NA | >97.5 |

[a]Not available.
[b]Also present was 2.0% by weight sodium dodecyl sulfate.
[c]In some cases, particularly with the addition of surfactant, cytopathic effects prevented useful data from being obtained. Such effects are described in Lennette, et al., Diagnostic Procedures for Viral, Rickettsial, and Chlamydial Infections, 1979, 5th Ed., p. 67.
[d]Wool substrate having a basis weight of 174.4 mg/in$^2$.
[e]Sodium dodecyl sulfate, 0.6 mg/in$^2$, was present on the substrate.
[f]Meltblown polypropylene face mask having a basis weight of 52.5 mg/in$^2$.

TABLE V

VIRUCIDAL ACTIVITY OF SULFAMIC ACID AGAINST RHINOVIRUS 16

| Example No. | sulfamic Acid Add-on Micromole/in$^2$ | Weight % | Surfactant Add-on Compound | Weight % | Virucidal Activity (% Inactivation) One min. | Five min. |
|---|---|---|---|---|---|---|
| 78 | 15.6 | 5 | — | — | 99 | >99.997 |
| 79 | 46.8 | 15 | — | — | 99.997 | >99.997 |
| 80 | 15.6 | 5 | — | — | 99 | 99 |
| 81 | 15.6 | 5 | SDS$^a$ | 2 | 99 | >99.99 |

$^a$Sodium dodecyl sulfate.

TABLE VI

NEUTRALIZATION OF ACTIVE INGREDIENTS BY PLACING THE ACTIVE INGREDIENTS (0–100 μl; 0.89 mmole/ml malic acid and 0.069 mmole/ml BIO-TERGE ® AS-40) IN NEUTRALIZING BROTH AND SUBSEQUENTLY ADDING THE MICROORGANISM

| Microorganism Tested | Quantities of Germicide (μl) 0 | 5 | 10 | 25 | 50 | 100 | Recovery$^c$ (%) |
|---|---|---|---|---|---|---|---|
| Staphylococcus aureus | +$^a$ | + | + | + | —$^b$ | — | 113 |
| Serratia marcescens | + | + | + | + | + | + | 100 |
| Candida albicans | + | + | + | + | + | — | 97 |

$^a$(+) designates growth of the test microorganism within the test tube after incubation for 24 hr.
$^b$(−) designates no growth of the test microorganism within the test tube after incubation for 24 hr.
$^c$designates percentage recovery of microorganisms after 15 min. exposure in the tubes containing 10 μl germicide in letheen broth.

TABLE VII

MINIMUM INHIBITORY CONCENTRATIONS OF MALIC ACID AND BIO-TERGE ® AS-40 AGAINST TWENTY-THREE FDA-DESIGNATED TEST MICROORGANISMS (10 MIN. CONTACT TIMES)

| Microorganism | ATCC Number | Concentrations Malic Acid μmol/ml | BIO-TERGE ® AS-40 μmol/ml |
|---|---|---|---|
| Gram Positive | | | |
| Micrococcus luteus | 9341 | 2.49 | 0.11 |
| Staphylococcus aureus | 6538 | 13.30 | 0.54 |
| Staphylococcus capitis | 27840 | 2.49 | 0.11 |
| Staphylococcus epidermidis | 12228 | 3.31 | 0.14 |
| Staphylococcus simulans | 27848 | 9.95 | 0.41 |
| Staphylococcus warneri | 27836 | 6.63 | 0.27 |
| Streptococcus C | 12388 | 0.83 | 0.035 |
| Streptococcus faecalis | 6569 | 3.31 | 0.14 |
| Streptococcus pyogenes | 12344 | 0.83 | 0.035 |
| Gram Negative | | | |
| Enterobacter aerogenes | 13048 | 13.30 | 0.54 |
| Enterobacter agglomerans | 29917 | 1.66 | 0.07 |
| Escherichia coli | 25922 | 6.63 | 0.27 |
| Klebsiella pneumoniae | 4352 | 1.66 | 0.07 |
| Morganella morganii | 25830 | 1.24 | 0.055 |
| Proteus mirabilis | 29906 | 3.31 | 0.14 |
| Providencia stuartii | 29914 | 13.30 | 0.54 |
| Pseudomonas aeruginosa | 15442 | 2.41 | 0.11 |
| Pseudomonas cepacia | 17765 | 6.63 | 0.27 |
| Salmonella cholerasuis | 10708 | 3.31 | 0.14 |
| Shigella sonnei | 11060 | 9.95 | 0.41 |
| Serratia marcescens | 13880 | 26.50 | 1.10 |
| Yeast | | | |
| Candida albicans | 10231 | 3.31 | 0.14 |
| Candida parapsilosis | 22019 | 1.66 | 0.07 |

TABLE VIII

LOTION FORMULATION

| Ingredients | Function | % by Weight |
|---|---|---|
| Malic Acid | Antimicrobial | 2.22–5.0 |
| BIO-TERGE ® AS-40 | Antimicrobial | 0.73–5.0 |
| HAMPOSYL ® L-30$^{a,b}$ | Fungicidal Agent | 0–10.0 |
| EMCOL 4072$^c$ | Thickener | 0–3.0 |
| Propylene glycol | Humectant | 5.0 |
| Ceteareth-20+ Ceteryl Alcohol | Emulsifier | 4.0 |
| Glyceryl Stearate-PEG-100 Stearate | Co-emulsifier | 1.0 |
| Propylene-glycol-Dioctanate | Emollient | 3.5 |
| Specially Denatured Ethyl-Alcohol$^a$ | — | 4.0 |
| Water | q.s. to 100 ml | |

$^a$Optional ingredient.
$^b$Sodium Lauroyl Sarcosinate 30% solution.
$^c$DERIPHAT food thickener can be substituted for this ingredient, depending upon aesthetic appeal.

TABLE IX

GERMICIDAL ACTIVITY OF LOTION CONTAINING MALIC ACID AND BIO-TERGE ® AS-40 IN SOLUTION AT LEVELS UP TO TEN TIMES THE MINIMUM INHIBITORY CONCENTRATION REQUIRED FOR GERMICIDAL ACTIVITY$^a$

| Test Microorganism | Concentrations of Malic Acid/Bio-Terge ® AS-40 (μmole/ml)/(μmole/ml) 331/58.1 | 165.5/29.0 | 82.75/14.52 | 41.3/7.26 | 20.68/3.63 | 10.34/1.81 | 5.17/0.91 |
|---|---|---|---|---|---|---|---|
| Candida albicans | — | + | + | + | + | + | + |
| Staphylococcus aureus | — | — | — | + | + | + | + |
| Serratia | — | — | — | + | + | + | + |

TABLE IX-continued

GERMICIDAL ACTIVITY OF LOTION CONTAINING MALIC ACID AND BIO-TERGE ® AS-40 IN SOLUTION AT LEVELS UP TO TEN TIMES THE MINIMUM INHIBITORY CONCENTRATION REQUIRED FOR GERMICIDAL ACTIVITY[a]

| Test Microorganism | Concentrations of Malic Acid/Bio-Terge ® AS-40 ($\mu$mole/ml)/($\mu$mole/ml) | | | | | | |
|---|---|---|---|---|---|---|---|
| | 331/ 58.1 | 165.5/ 29.0 | 82.75/ 14.52 | 41.3/ 7.26 | 20.68/ 3.63 | 10.34/ 1.81 | 5.17/ 0.91 |
| *marcescens* | | | | | | | |

[a]M.I.C. testing methodology was employed for a 10-minute exposure time. In the table, a + designates growth of the test microorganism within the test tube after incubation for 24 hours, whereas a − designates no growth after the same period of time.

TABLE X

GERMICIDAL ACTIVITY OF LOTION CONTAINING MAXIMUM FORMULA CONCENTRATIONS OF MALIC ACID AND BIO-TERGE ® AS-40[a]

| Test Microorganism | Concentrations of Malic Acid/Bio-Terge ® AS-40 ($\mu$mole/ml)/($\mu$mole/ml) | | | | | | |
|---|---|---|---|---|---|---|---|
| | 372/ 145[b] | 186/ 72.5 | 93/ 36.25 | 46.5/ 18.12 | 23.25/ 9.06 | 11.62/ 4.53 | 5.81/ 2.26 |
| *Candida albicans* | − | − | − | + | + | + | + |
| *Staphylococcus aureus* | − | − | − | − | − | + | + |
| *Serratia marcescens* | − | − | − | − | + | + | + |

[a]M.I.C. testing methodology was employed for a 10-minute exposure time. In the table, a + designates growth of the test microorganism within the test tube after incubation for 24 hours, whereas a − designates no growth after the same period of time.
[b]The maximum concentrations of acid and surfactant, respectively, which could be emulsified and remain stable.

TABLE XI

SOAP FORMULATION

| Ingredients[a] | Function | % by Weight |
|---|---|---|
| Malic Acid | Antimicrobial | 4.44 |
| BIO-TERGE ® AS-40 | Antimicrobial | 2.00 |
| HAMPOSYL ® L-30[b] | Fungicidal Agent | 10.1 |
| PEG-80-Sorbitan Laurate | Minimizes Irritation | 10.0 |
| Nonylphenol-9 units of ethylene oxide methyl-carboxylate[c] | Foaming | 20.0 |
| Sodium-N-Cocoyl-N-Methyl Taurate | Builds Viscosity | 20.0 |
| $C^{12-15}$ Alcohol Benzoate | Emollient | 3.0 |
| Mineral Oil | Humectant | 1.5 |
| Ammonium Chloride | Maintain Viscosity | 1.0 |
| Water | | q.s. to 100 ml |

[a]Although the formulation has a high concentration of solids, adjustments may be made to the concentrations employed.
[b]Sodium Lauroyl Sarcosinate (30.0%)
[c]SURFINE AZI-A, Finetex, Inc., Elmwood Park, New Jersey.

TABLE XII

IN VITRO TEST OF EFFICACY OF GERMICIDAL SOAP[a]

| Concentrations | | Test Microorganism | | |
|---|---|---|---|---|
| Malic Acid ($\mu$mol/ml) | BIO-TERGE ® AS-40 ($\mu$mol/ml) | Candida albicans | Staphylococcus aureus | Serratia marcescens |
| 372 | 145 | − | − | − |
| 186 | 72.5 | + | − | − |
| 93 | 36.25 | + | − | − |
| 46.5 | 18.12 | + | − | − |
| 23.25 | 9.06 | + | − | − |
| 11.62 | 4.53 | + | − | − |
| 5.81 | 2.26 | + | − | + |
| 2.90 | 1.13 | + | − | + |
| 1.45 | 0.56 | + | + | + |
| 0.73 | 0.28 | + | + | + |

+ Designates growth of the test microorganism within the test tube after incubation for 24 hrs.
− Designates no growth of the test microorganism within the test tube after incubation for 24 hrs.
[a]M.I.C. testing methodology employed with 10 min. exposure time.

TABLE XIII

IN VIVO GERMICIDAL ACTIVITY OF ANTIMICROBIALS AGAINST APPLIED SERRATIA MARCESCENS (20 HAND WASHES)

| | Lotion Without Actives | Lotion With Actives[a] | HIBICLENS ® |
|---|---|---|---|
| Log Mean Survivors on Untreated Skin | 7.3 | 8.2 | 8.0 |
| Log Mean Survivors After 60 Sec. Treatment | 6.8 | 6.9 | 5.4 |
| Log Reduction (± S.D.) | 0.5 ± 0.3 | 1.3 ± 0.3 | 2.6 ± 0.6 |

[a]Germicidal lotion contains 2.22% w/v malic acid and 0.73% v/v BIO-TERGE ® AS-40 and the other ingredients listed in Table VIII, except for HAMPOSYL ® L-30 and specially denatured ethyl alcohol.

TABLE XIV

IN VIVO GERMICIDAL ACTIVITY OF ANTIMICROBIALS AGAINST APPLIED SERRATIA MARCESCENS (20 HAND WASHES)

| | Lotion Vehicle | Lotion 1[a] | Lotion 2[b] | HIBICLENS ® |
|---|---|---|---|---|
| Log Mean Survivors on Untreated Skin | 7.3 | 8.0 | 7.3 | 8.0 |
| Log Mean Survivors After 60 Sec. Treatment | 6.8 | 5.7 | 5.2 | 5.4 |
| Log Reduction (± S.D.) | 0.5 ± 0.3 | 2.3 ± 0.5 | 2.1 ± 0.3 | 2.6 ± 0.6 |

[a]Lotion composed of malic acid (5.0% w/v), BIO-TERGE ® AS-40 (5.0% v/v), HAMPOSYL ® L-30 (10.0% v/v), specially denatured ethyl alcohol (4.0% v/v) and the other ingredients listed in Table VIII.
[b]Lotion composed of malic acid (4.44% w/v), BIO-TERGE ® AS-40 (2.0% v/v), HAMPOSYL ® L-30 (10.0% v/v), specially denatured ethyl alcohol (4.0% v/v) and the other ingredients listed in Table VIII.

TABLE XV

GERMICIDAL ACTIVITY AGAINST APPLIED *SERRATIA MARCESCENS*

| | Lotion 1[a] | Lotion 2[b] | EPICARE ® | Accent Plus-One |
|---|---|---|---|---|
| Log Mean Survivors on Untreated Skin | 8.0 | 7.3 | 7.9 | 7.9 |
| Log Mean Survivors After 60 Sec. Treatment | 5.7 | 5.2 | 5.6 | 7.6 |
| Log Reduction (± S.D.) | 2.3 ± 0.5 | 2.1 ± 0.3 | 2.3 ± 0.6 | 0.3 ± 0.3 |

[a]Lotion composed of malic acid (5.0% w/v), BIO-TERGE ® AS-40 (5.0% v/v), HAMPOSYL ® L-30 (10.0% v/v), specially denatured ethyl alcohol (4.0% v/v) and the other ingredients listed in Table VIII.
[b]Lotion composed of malic acid (4.44% w/v), BIO-TERGE ® AS-40 (2.0% v/v), HAMPOSYL ® L-30 (10.0% v/v), specially denatured ethyl alcohol (4.0% v/v) and the other ingredients listed in Table VIII.

TABLE XVI

GERMICIDAL ACTIVITY AGAINST APPLIED *SERRATIA MARCESCENS* (20 DETERMINATIONS)

| | Soft Soap[a] | Germicidal Soap[b] | HIBICLENS ® |
|---|---|---|---|
| Log Mean Survivors on Untreated Skin | 8.2 | 8.2 | 7.9 |
| Log Mean Survivors After 60 Sec. Treatment | 8.0 | 5.9 | 5.1 |
| Log Reduction (± S.D.) | 0.2 ± 0.1 | 2.3 ± 0.3 | 2.8 ± 0.3 |

[a]Soap without Antimicrobial Ingredients.
[b]See Table XI.

What is claimed is:

1. A germicidal composition for direct application to human skin consisting essentially of an alkyl sulfonate salt and an organic acid selected from the group consisting of malic acid, citric acid, and mixtures thereof, the alkyl sulfonate salt and the organic acid being the sole active ingredients in the composition, and an aqueous vehicle for administering the alkyl sulfonate salt and the organic acid to human skin, the concentrations of the alkyl sulfonate salt and the organic acid being sufficient to render the composition germicidally effective.

2. A germicidal composition for direct application to human skin consisting essentially of an alkyl sulfonate salt, an alcohol, and an organic acid selected from the group consisting of malic acid, citric acid, and mixtures thereof, the alkyl sulfonate salt, the alcohol, and the organic acid being the sole active ingredients in the composition, and an aqueous vehicle for administering the alkyl sulfonate salt, alcohol and organic acid to human skin, the concentrations of the alkyl sulfonate salt, alcohol and organic acid being sufficient to render the composition germicidally effective.

3. The germicidal composition of claims 1 or 2 wherein the organic acid is malic acid.

4. The germicidal composition of claims 1 or 2 wherein the alkyl sulfonate salt is an alpha-olefin sulfonate salt.

5. The germicidal composition of claim 4 wherein the alpha-olefin sulfonate salt has between about 8 and about 18 carbon atoms.

6. The germicidal composition of claim 5 wherein the alpha-olefin sulfonate salt has between about 12 and about 16 carbon atoms.

7. The germicidal composition of claims 1 or 2 wherein the organic acid is malic acid and the alkyl sulfonate salt is an alpha-olefin salt.

8. The germicidal composition of claim 2 wherein the alcohol is ethyl alcohol.

9. The germicidal composition of claim 8 wherein the organic acid is malic acid and the alkyl sulfonate slat is an alpha-olefin sulfonate salt.

10. The germicidal composition of claims 1 or 2 wherein said composition is in the form of a lotion.

11. The germicidal composition of claim 10 wherein the concentration of the organic acid is between about 0.1% w/v and about 10% w/v and the concentration of the alkyl sulfonate salt is between about 0.1% v/v and about 10% v/v.

12. The germicidal composition of claim 11 wherein the concentration of the organic acid is between about 2% w/v and about 7% w/v and the concentration of the alkyl sulfonate salt is between about 0.5% v/v and about 7% v/v.

13. The germicidal composition of claim 2 in the form of a lotion wherein the composition further includes an alcohol as an active ingredient and the concentration of the alcohol is between about 0.5% v/v and about 10% v/v.

14. The germicidal composition of claim 13 wherein the concentration of the alcohol is between about 2% v/v and about 6% v/v.

15. The germicidal composition of claims 1 or 2 wherein said composition is in the form of a soap.

16. The germicidal composition of claim 15 wherein the concentration of the organic acid is between about 0.1% w/v and about 10% w/v and the concentration of the alkyl sulfonate salt is between about 0.1% v/v and about 60% v/v.

17. The germicidal composition of claim 16 wherein the concentration of the organic acid is between about 2% w/v and about 7% w/v and the concentration of the alkyl sulfonate salt is between about 2% v/v and about 55% v/v.

18. The germicidal composition of claim 2 in the form of a soap wherein the composition further includes an alcohol as an active ingredient and the concentration of the alcohol is between about 0.5% v/v and about 10% v/v.

19. The germicidal composition of claim 18 wherein the concentration of the alcohol is between about 2% v/v and about 6% v/v.

20. The germicidal composition of claims 1 or 2 wherein the pH of the composition is between about 2.0 and about 4.0.

* * * * *